US00PP30862P3

(12) United States Plant Patent
Sundermeyer

(10) Patent No.: US PP30,862 P3
(45) Date of Patent: Sep. 3, 2019

(54) APPLE TREE NAMED 'GS-66'

(50) Latin Name: *Malus domestica*
Varietal Denomination: GS 66

(71) Applicant: Deutsches Obstsorten Konsortium GmbH, Hollern Twielenfleth (DE)

(72) Inventor: Gerhard Sundermeyer, Wendhausen (DE)

(73) Assignee: Deutsches Obstsorten Konsortium GmbH, Hollern Twielenfleth (DE)

( * ) Notice: Subject to any disclaimer, the term of this patent is extended or adjusted under 35 U.S.C. 154(b) by 0 days.

(21) Appl. No.: 15/732,721

(22) Filed: Dec. 18, 2017

(65) Prior Publication Data

US 2019/0191609 P1 Jun. 20, 2019

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418; A01H 5/08
See application file for complete search history.

*Primary Examiner* — Keith O. Robinson
(74) *Attorney, Agent, or Firm* — Michelle Bos Legal LLC

(57) ABSTRACT

'GS 66' is a new apple tree variety notable for its fruit. Apples of 'GS 66' exhibit a shiny red overcolor, crisp juicy non-browning flesh, and resistance to bruising.

4 Drawing Sheets

Latin name: *Malus domestica.*
Variety denomination: 'GS 66'.

BACKGROUND OF THE VARIETY

'GS 66' is a new and distinct variety of apple tree (*Malus domestica*) of unknown parentage. 'GS 66' originated from an open cross in 2008 in a commercial orchard at Wendhausen, Germany in 2008, and was identified by the inventor as a candidate for further evaluation in 2012. 'GS 66' was first asexually reproduced by table grafting at Wendhausen, Germany in 2013, and has since been observed to remain true to type over successive asexually propagated generations.

BRIEF DESCRIPTION OF THE VARIETY

'GS 66' was first selected for its shiny red overcolor and dominant lenticels, crisp juicy non-browning flesh, and resistance to bruising. Comparisons of 'GS 66' to similar varieties are shown in the following table.

TABLE 1

Comparison of 'GS 66' to Similar Varieties

| | 'GS 66' | 'Braeburn'* | 'Minneiska'* | 'Elstar'* |
|---|---|---|---|---|
| Fruit size | Large | Medium | Large | Medium |
| Crispness | High | Low | High | Medium |
| Shelf-life | Very good | Good | Good | Medium |
| Firmness | High | High | Medium | Medium |
| Ripening time | Late | Late | Early | Medium |

*'Braeburn' - not patented; 'Minneiska' - U.S. Plant Pat. No. 18812; 'Elstar' - U.S. Plant Pat. No. 6450

BRIEF DESCRIPTION OF THE PHOTOGRAPHS

The appended photographs, taken in 2017 at Wendhausen, Germany, show 8-year-old trees grown on 'M9' rootstock (not patented).

Figure 1:
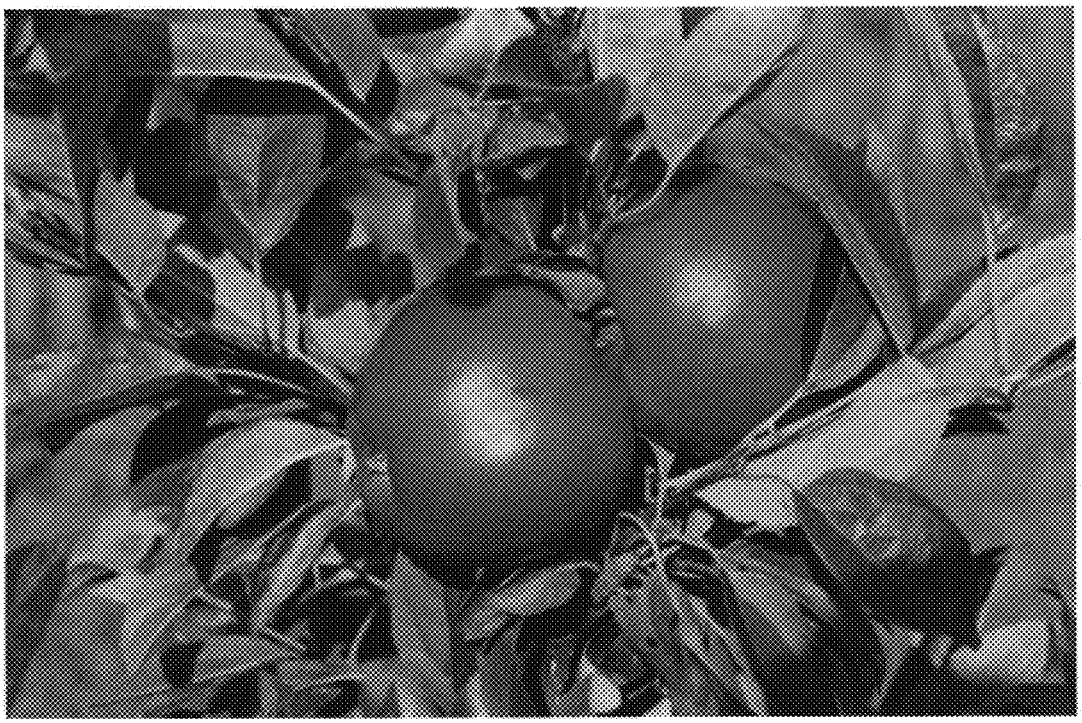
Figure 2:
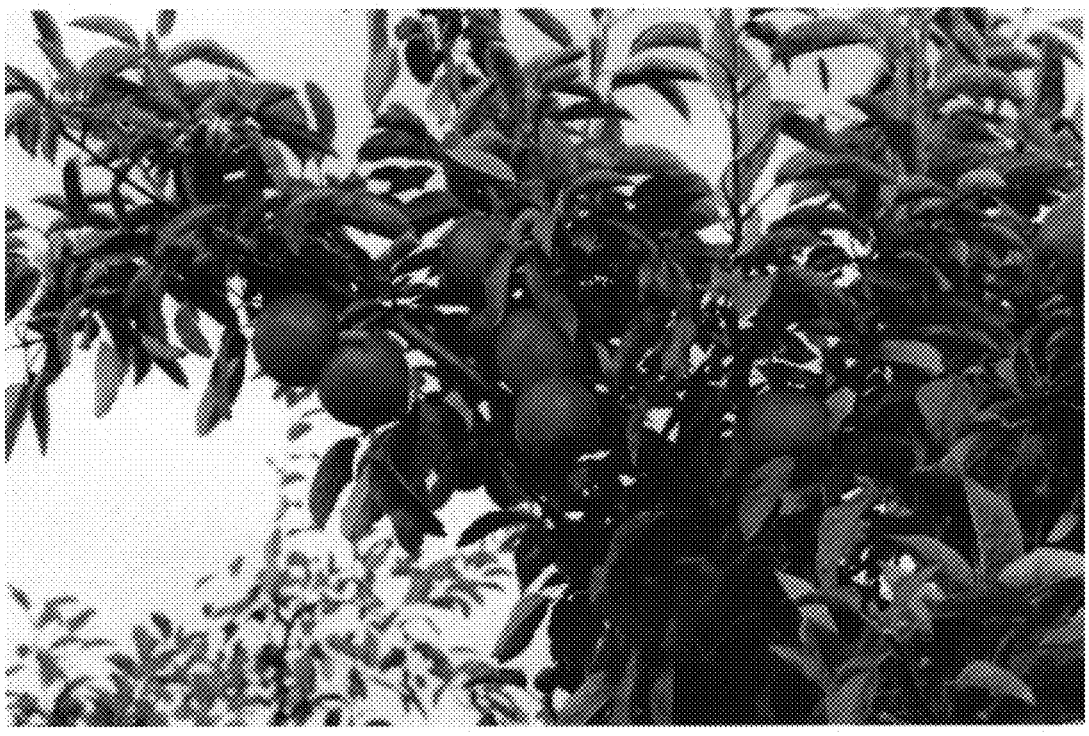
Figure 3:
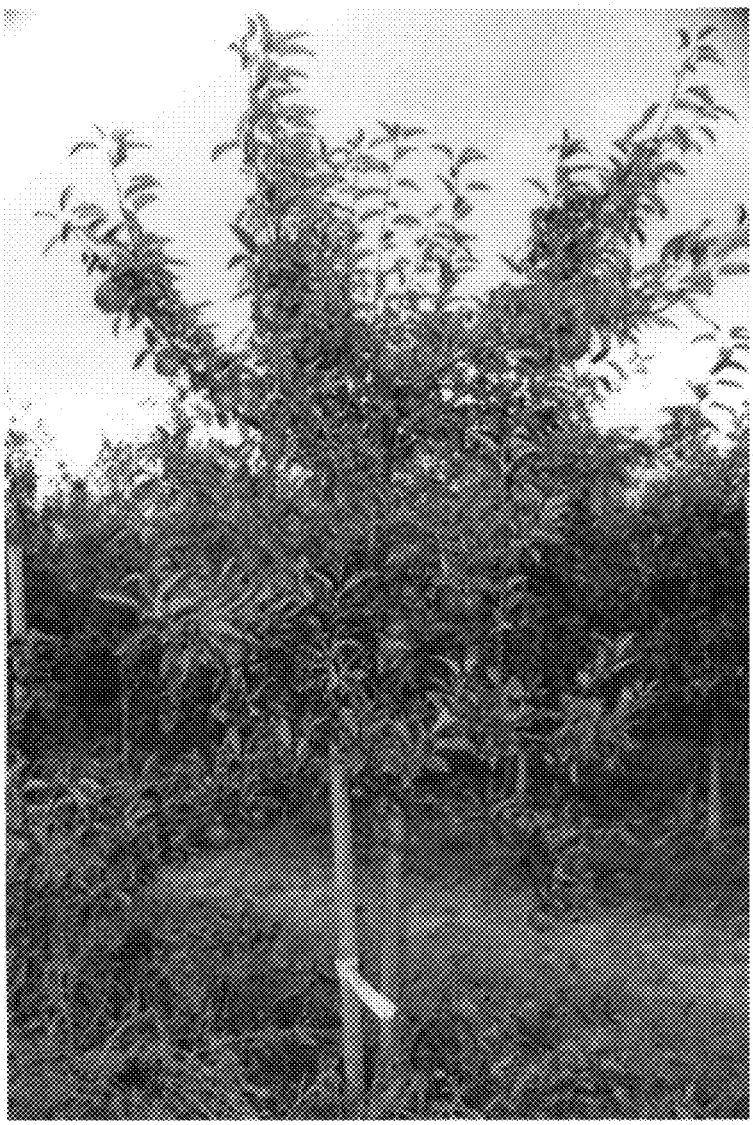
Figure 4:
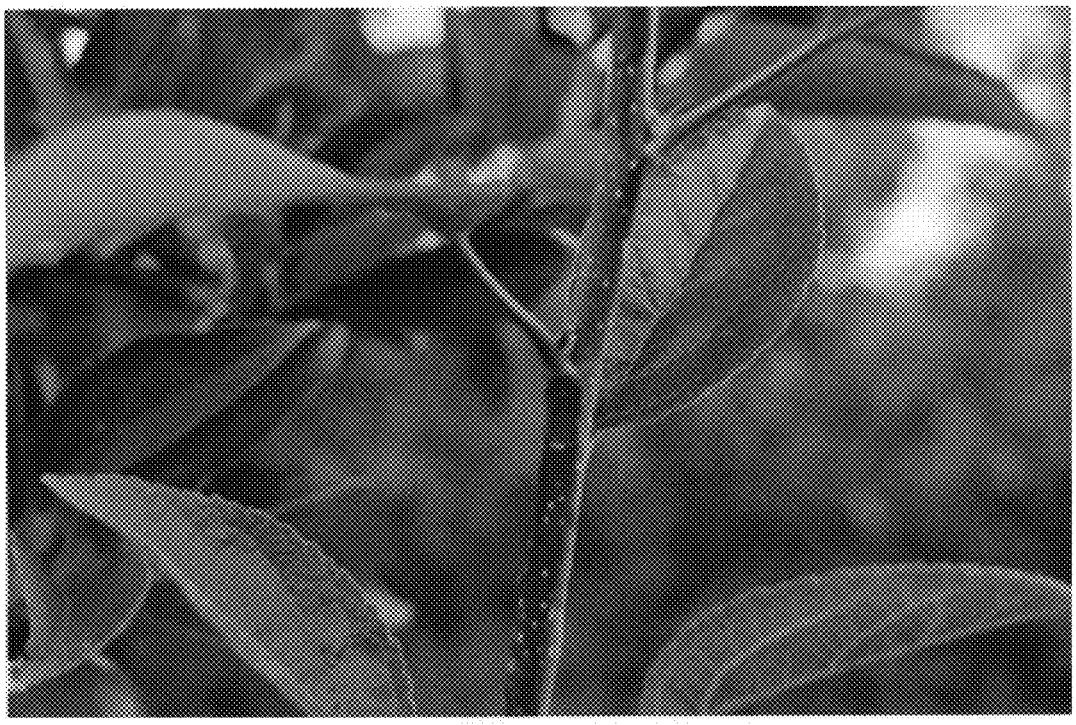

FIG. 1 shows fruit and leaves of 'GS 66';
FIG. 2 shows fruit, leaves and branches of a 'GS 66' tree;
FIG. 3 shows a 'GS 66' tree; and,
FIG. 4 shows leaves of 'GS 66'.

DETAILED BOTANICAL DESCRIPTION OF THE VARIETY

The following-detailed botanical description is based on observations made during 2017 at Wendhausen, Germany of 8-year-old trees grown on 'M9' rootstock (not patented). All colors are described according to The Royal Horticultural Society Colour Chart (1966 edition). It should be understood that the characteristics described will vary somewhat depending upon cultural practices and climatic conditions, and will vary with location and season. Quantified measurements are expressed as an average of measurements taken. The measurements of any individual plant or any group of plants of the new variety may vary from the stated average.

Tree:
*Vigor.*—Medium.
*Type.*—Ramified.
*Habit.*—Spreading.
*Height.*—3.5 m.
*Bearing.*—On shoots and spurs.
*Trunk diameter* (*at* 30 *cm above the graft*).—73 mm.
*Bark texture.*—Smooth.
*Bark coloration.*—Greyed-orange 175C.
*Lenticel length.*—10 to 13 mm.
*Lenticel color.*—Yellow-white 158D.

Branch (fruiting branches located at around 1 m above the graft union):
*Length.*—70 to 90 cm.
*Diameter.*—21 mm on a 90 cm branch.
*Crotch angle.*—85°.
*Bark color.*—Greyed-orange 177B.
*Lenticel length.*—9 to 12 mm.

*Lenticel color*.—Yellow-white 158D.
*Lenticel quantity*.—5 to 6 per $cm^2$.

One year old shoot:
*Length*.—20 to 25 cm.
*Diameter*.—5 to 6 mm.
*Color*.—Brown 200A.
*Pubescence*.—None to low.
*Internode length*.—25 to 27 mm.
*Lenticel quantity*.—6 to 7 per $cm^2$.
*Lenticel color*.—Orange-white 159B.

Flower buds:
*Quantity per spur*.—1.
*Shape*.—Conical.
*Apex*.—Pointed.
*Length*.—15 mm.
*Diameter*.—5 to 7 mm.
*Color*.—Greyed-orange 177A.

Flowers:
*Diameter*.—4.3 cm.
*Color*.—White 155B with purple 74C veins.
*Petal arrangement*.—Not touching.
*Flowers per cluster*.—6 to 7.
*Time of beginning of flowering*.—First bloom April 21, full bloom April 28; 3 days after 'Golden Delicious' (not patented).

Petals:
*Quantity per flower*.—5.
*Length*.—18 mm to 21 mm.
*Diameter*.—12 mm to 14 mm.
*Shape*.—Oval.
*Apex shape*.—Rounded.
*Base*.—Pointed.
*Margin*.—Smooth.

Pedicel:
*Length*.—25 mm to 28 mm.
*Diameter*.—1 mm to 1.2 mm.
*Color*.—Yellow green 144B.

Sepals:
*Quantity*.—5.
*Shape*.—Pointed conical.
*Apex shape*.—Acute.
*Margin*.—Smooth.

Leaves:
*Shape*.—Elliptic to oval.
*Length*.—90 to 100 mm.
*Width*.—45 to 50 mm.
*Length/width ratio*.—2:1.
*Blade margin*.—Crenate.
*Apex*.—Acuminate.
*Base shape*.—Rounded.
*Color of upper surface*.—Green 138A.
*Color of lower surface*.—Green 138B.
*Attitude in relation to shoot*.—Upward.

Petiole:
*Length*.—25 to 29 mm.
*Diameter*.—1.5 mm.
*Color*.—Greyed-purple 184D.

Fruit:
*Quantity per cluster*.—1 to 2.
*Diameter*.—70 to 80 mm.
*Height*.—80 mm.
*Weight*.—239 g.
*Ratio of height to width*.—1:0.97.
*General shape in profile*.—Globose.
*Position of maximum diameter*.—Upper third to middle.
*Ribbing*.—Absent or weak.
*Crowning at calyx end*.—Low.
*Bloom of skin*.—None.
*Greasiness of skin*.—Absent or weak.
*Over color of skin*.—Greyed-red 179A.
*Intensity of over color*.—Dark.
*Amount of over color*.—70 to 80%.
*Pattern of over color*.—Solid flush with weakly defined stripes; some minor stripes on shaded side.
*Background color of skin*.—Greyed-yellow 160A.
*Lenticels*.—Prominent, abundant.
*Amount of russet around stalk cavity*.—Low; low-medium inside stalk cavity.
*Amount of russet on cheeks*.—None.
*Area of russet around eye basin*.—None.
*Length of stalk*.—20 mm.
*Thickness of stalk*.—2.2 mm.
*Depth of stalk cavity*.—17 mm.
*Width of stalk cavity*.—23 mm.
*Depth of eye basin*.—12 mm.
*Width of eye basin*.—19 mm.
*Aperture of eye*.—Closed.
*Size of eye*.—Small, about 3 mm to 4 mm.
*Length of sepal*.—6 mm.
*Firmness of flesh*.—Firm, 8.2 $kg/cm^2$.
*Flesh texture*.—Very crisp, fine.
*Juiciness*.—High.
*Brix*.—13.7° Brix.
*Acidity*.—8.9%.
*Flesh color*.—Greyed-yellow 160D.
*Stem color*.—Greyed-orange 174B.

Seeds:
*Quantity per fruit*.—6.
*Shape*.—Oval.
*Color*.—Greyed-orange 175A.
*Size*.—Length 9 mm; width 4.8 mm.

Harvest:
*Time for harvest*.—Similar to 'Braeburn'; Oct. 15, 2017.
*Number of picks*.—Two.
*Fruit load per tree*.—63 (frost at test site in 2017).

Disease resistance/susceptibility: Susceptible to mildew (*Podosphaera leucotricha*).

Storage characteristics: Very good, more than 4 months in cold storage; more than 7 months in controlled atmosphere storage.

Market use: Fresh consumption.

I claim:

1. A new and distinct apple tree substantially as described and illustrated herein.

* * * * *